US006946852B2

(12) United States Patent
Centanni

(10) Patent No.: US 6,946,852 B2
(45) Date of Patent: Sep. 20, 2005

(54) METHOD AND APPARATUS FOR MEASURING CONCENTRATION OF A CHEMICAL COMPONENT IN A GAS MIXTURE

(75) Inventor: Michael A. Centanni, Parma, OH (US)

(73) Assignee: Steris Inc., Temecula, CA (US)

( * ) Notice: Subject to any disclaimer, the term of this patent is extended or adjusted under 35 U.S.C. 154(b) by 108 days.

(21) Appl. No.: 10/405,880

(22) Filed: Apr. 2, 2003

(65) Prior Publication Data

US 2004/0178803 A1 Sep. 16, 2004

Related U.S. Application Data

(63) Continuation-in-part of application No. 10/389,036, filed on Mar. 14, 2003.

(51) Int. Cl.[7] ............................................... G01R 27/26
(52) U.S. Cl. ....................................... 324/663; 324/666
(58) Field of Search ......................... 324/664, 658–666; 210/96.1, 754; 436/124, 125

(56) References Cited

U.S. PATENT DOCUMENTS

| | | | |
|---|---|---|---|
| 3,636,444 A | 1/1972 | Strawn et al. ............. 324/61 R |
| 3,778,706 A | 12/1973 | Thompson ................ 324/61 R |
| 3,816,811 A | 6/1974 | Cmelik ..................... 324/61 R |
| 4,031,742 A | * | 6/1977 | Michael et al. .............. 73/40.7 |
| 4,158,810 A | 6/1979 | Leskovar ..................... 324/127 |
| 4,219,776 A | 8/1980 | Arulanandan ............... 324/323 |
| 4,427,772 A | 1/1984 | Kodera et al. ................. 435/27 |
| 4,509,522 A | * | 4/1985 | Manuccia et al. ........... 600/326 |
| 4,525,265 A | 6/1985 | Abe et al. .................... 204/403 |
| 4,674,879 A | 6/1987 | Gregorig et al. ............. 356/301 |
| 4,769,593 A | 9/1988 | Reed et al. .................. 324/668 |
| 4,849,687 A | 7/1989 | Sims et al. .................. 324/668 |
| 4,857,152 A | 8/1989 | Armstrong et al. ......... 204/1 T |
| 5,151,660 A | 9/1992 | Powers et al. .............. 324/689 |
| 5,157,968 A | 10/1992 | Zfira ............................ 73/149 |
| 5,171,523 A | 12/1992 | Williams ....................... 422/20 |
| 5,179,926 A | * | 1/1993 | Ament ........................ 123/494 |
| 5,243,858 A | 9/1993 | Erskine et al. ........... 73/204.26 |
| 5,364,510 A | 11/1994 | Carpio ..................... 204/153.1 |
| 5,439,569 A | 8/1995 | Carpio ..................... 204/153.1 |
| 5,459,568 A | 10/1995 | Yano et al. .................. 356/336 |
| 5,470,754 A | 11/1995 | Rounbehler et al. ......... 436/106 |
| 5,600,142 A | 2/1997 | Van Den Berg et al. ...................... 250/339.13 |
| 5,847,276 A | 12/1998 | Mimken et al. .............. 73/453 |
| 5,861,303 A | 1/1999 | Barshter et al. ............. 435/266 |
| 5,882,590 A | 3/1999 | Stewart et al. ................ 422/28 |

(Continued)

OTHER PUBLICATIONS

U.S. Appl. No. 10/872,227, filed Jun. 18, 2004, Kaiser et al., entitled: Method and Apparatus for Monitoring the Purity and/or Quality of Steam.

(Continued)

Primary Examiner—Anjan Deb
Assistant Examiner—Amy He
(74) Attorney, Agent, or Firm—Kusner & Jaffe; Michael A. Centanni

(57) ABSTRACT

A chemical concentration detecting system for determining the relative concentration of a chemical component in a gas mixture. The gas mixture may include chemical components that are antimicrobial chemicals, as well as chemical components that are base chemicals, acting as a diluent for the antimicrobial chemical, or as a vehicle or carrier for the antimicrobial chemical. A capacitor is exposed to the gas mixture, wherein the gas mixture acts as a dielectric between the plates of the capacitor. Permittivity of the dielectric is affected by the relative concentrations of the chemical components, and thus a measurement of the capacitance is used to determine the relative concentration levels of the chemical components in the gas mixture.

31 Claims, 2 Drawing Sheets

U.S. PATENT DOCUMENTS

| | | | | |
|---|---|---|---|---|
| 5,997,685 | A | 12/1999 | Radhamohan et al. | 156/345 |
| 6,162,409 | A | 12/2000 | Skelley et al. | 423/239.1 |
| 6,369,387 | B1 | 4/2002 | Eckles | 250/343 |
| 6,454,874 | B1 | 9/2002 | Jacobs et al. | 134/18 |
| 6,614,242 | B2 | 9/2003 | Matter et al. | 324/698 |
| 6,660,231 | B2 * | 12/2003 | Moseley | 422/98 |
| 6,706,648 | B2 | 3/2004 | Yamazaki et al. | 438/790 |
| 2002/0014410 | A1 * | 2/2002 | Silveri et al. | 204/412 |
| 2002/0033186 | A1 | 3/2002 | Verhaverbeke et al. | 134/26 |
| 2002/0076492 | A1 | 6/2002 | Loan et al. | 427/255.28 |
| 2002/0109511 | A1 | 8/2002 | Frank | 324/663 |
| 2002/0111040 | A1 | 8/2002 | Yamazaki et al. | 438/783 |
| 2002/0157686 | A1 | 10/2002 | Kenny et al. | 134/1.3 |
| 2003/0063997 | A1 | 4/2003 | Fryer et al. | 422/3 |
| 2003/0102007 | A1 | 6/2003 | Kaiser | 134/1 |
| 2003/0157587 | A1 | 8/2003 | Gomez et al. | 435/30 |
| 2004/0029257 | A1 | 2/2004 | Dutil et al. | 435/266 |
| 2004/0079395 | A1 | 4/2004 | Kim et al. | 134/30 |
| 2004/0178799 | A1 | 9/2004 | Korenev et al. | 324/453 |
| 2004/0178802 | A1 | 9/2004 | Centanni | 324/662 |
| 2004/0178804 | A1 | 9/2004 | Allen et al. | 324/662 |
| 2004/0262170 | A1 | 12/2004 | Centanni | 205/782 |

OTHER PUBLICATIONS

U.S. Appl. No. 10/896,609, filed Jul. 21, 2004, Kaiser et al., entitled: Method and Apparatus for Real Time Monitoring of Metallic Cation Concentrations in a Solution.

U.S. Appl. No. 10/900,745, filed Jul. 28, 2004, Kaiser et al., entitled: Method and Apparatus for Monitoring the State of a Chemical Solution for Decontamination of Chemical and Biological Warfare Agents.

U.S. Appl. No. 10/931,186, filed Aug. 31, 2004, Kaiser et al., entitled: Method and Apparatus for Monitoring Detergent Concentration in a Decontamination Process.

U.S. Appl. No. 10/456,378, filed Jun. 6, 2003, Centanni, entitled: Method and Apparatus for Formulating and Controlling Chemical Concentrations in a Solution.

U.S. Appl. No. 10/456,380, filed Jun. 6, 2003, Centanni, entitled: Method and Apparatus for Formulating and Controlling Chemical Concentrations in a Gas Mixture.

U.S. Appl. No. 10/667,988, filed Sep. 22, 2003, Korenev et al., entitled: Method and Apparatus for Measuring the Concentration of Hydrogen Peroxide in a Fluid.

T. J. Buckley et al., "*Toroidal Cross Capacitor for Measuring the Dielectric Constant of Gases*," Review of Scientific Instruments, vol. 71, No. 7, Jul. 2000, pp. 2914–2921.

Gross et al., "*The Dielectric Constants of Water Hydrogen Peroxide and Hydrogen Peroxide–Water Mixtures*," L. Amer. Chem. Soc., vol. 72, 1950, pp. 2075–2080.

"*Humidity Sensor Theory and Behavior*," Psychometrics and Moisture, Honeywell HVAC, Nov. 27, 2002.

Philipp, "*Charge Transfer Sensing*," 1997.

Wojslaw, "*Everything You Wanted to Know About Digitally Programmable Potentiometers*," Catalyst Semiconductor, Inc., Oct. 17, 2001, Publication No. 6009.

Kittel, "*Introduction to Solid State Physics*," Fourth Edition, John Wiley & Sons, Inc., 1971.

Philipp, "*The Charge Transfer Sensor*," Sensors Magazine, Oct. 1999.

* cited by examiner

METHOD AND APPARATUS FOR MEASURING CONCENTRATION OF A CHEMICAL COMPONENT IN A GAS MIXTURE

RELATED APPLICATIONS

The present invention is a Continuation-In-Part (CIP) of U.S. application Ser. No. 10/389,036, filed Mar. 14, 2003, entitled "Method and Apparatus for Measuring Chemical Concentration in a Fluid," which is incorporated herein by reference in its entirety.

FIELD OF THE INVENTION

The present invention relates to determining chemical concentrations, and more particularly to a method and apparatus for measuring the concentration of a chemical component in a gas mixture.

BACKGROUND OF THE INVENTION

The degree of polarity of a molecule is expressed in terms of a "dipole moment." Molecules, such as water, that exhibit a separation of charge within the molecule, have non-zero dipole moments. If the separated charges are equal in magnitude but opposite in sign, the magnitude of the dipole moment is equal to the product of the value of one of the separated charges and the distance of separation between the charges. The dipole moment is a vector that points from the negatively charged side of the molecule to the positively charged side of the molecule. The dipole moment depends on three factors, namely, (1) polarity of the molecule, (2) the magnitude of the separated charge, and (3) the geometry of the molecule. It is known that different molecules will have different dipole moments. For instance, molecules of antimicrobial chemicals, such as ozone ($O_3$), and hydrogen peroxide ($H_2O_2$), have different dipole moments than molecules of water ($H_2O$).

The present invention uses differences in the dipole moments of different molecules as a means for determining the concentration of a chemical component in a gas mixture.

SUMMARY OF THE INVENTION

In accordance with the present invention, there is provided a chemical concentration detecting system for determining a concentration of a first chemical component in a gas mixture, comprising: (1) a capacitor having first and second plates exposed to the gas mixture, said gas mixture being a dielectric therebetween; and (2) processing means for determining a change in an electrical property of the capacitor, said change in the electrical property varying according to the concentration of the first chemical component in the gas mixture.

In accordance with another aspect of the present invention, there is provided a method for determining a concentration of a first chemical component in a gas mixture, comprising: (1) exposing a capacitor, having first and second parallel plates, to the gas mixture, said gas mixture comprising a dielectric therebetween; and (2) determining a change in an electrical property of the capacitor, said change in the electrical property varying according to the concentration of the first chemical component in the gas mixture.

An advantage of the present invention is the provision of a concentration measuring system that uses a gas mixture as a dielectric of a capacitor.

Another advantage of the present invention is the provision of a concentration measuring system that will measure the concentration of a wide variety of chemical components, including antimicrobial chemicals.

Still another advantage of the present invention is the provision of a concentration measuring system that provides an accurate measurement of the concentration of a chemical component in a gas mixture.

Yet another advantage of the present invention is the provision of a concentration measuring system that is simple and inexpensive to manufacture.

These and other advantages will become apparent from the following description of a preferred embodiment taken together with the accompanying drawings and the appended claims.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein.

DETAILED DESCRIPTION OF A PREFERRED EMBODIMENT

Figure 1:
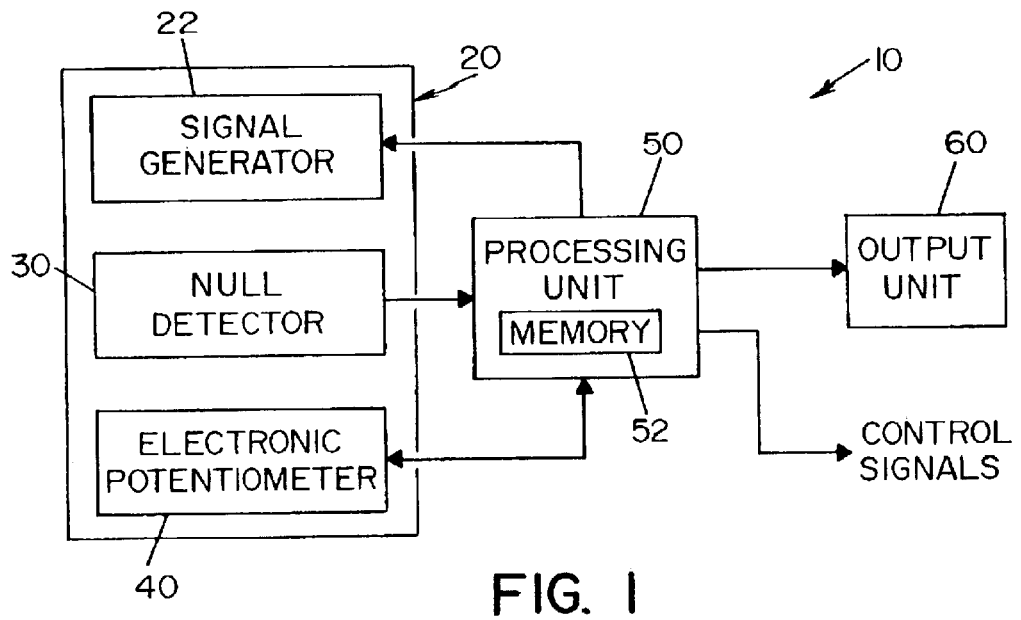
FIG. 1 is a block diagram of a chemical concentration detecting system, according to a preferred embodiment of the present invention.

Referring now to the drawings wherein the showings are for the purposes of illustrating a preferred embodiment of the invention only and not for purposes of limiting same, FIG. 1 shows a chemical concentration detecting system 10 according to a preferred embodiment of the present invention. Detecting system 10 is generally comprised of a sensor circuit 20, a processing unit 50 and an output unit 60.

Sensor circuit 20 uses a capacitor to sense concentration of a chemical component in a gas mixture inside a chamber 100, as will be described in detail below. In this regard, it should be appreciated that the dielectric constant of a capacitor is dependent on electronic "polarizability." Polarization is the ability of molecules to form a dipole under an electric field or the ability of the electric field to line up or rotate an inherent dipole, such as water molecules.

It should be understood that the term "gas," as used herein, includes (a) chemical components that are gases at room temperature, and (b) chemical components that are in a vapor phase due to vaporization of a liquid.

In a preferred embodiment, the gas mixture includes at least one chemical component that is a decontaminant or sterilant, such as an antimicrobial chemical. Antimicrobial chemicals are active chemicals for a decontamination or sterilization process. The gas mixture may also include at least one chemical component that is "base" chemical. Base chemicals act as a diluent for an antimicrobial chemical, or as a vehicle or carrier for an antimicrobial chemical. The gas mixture also typically includes air as a chemical component. It is contemplated by the inventor that the gas mixture may include chemical components not specifically identified herein, as well as chemical components unrelated to a decontamination or sterilization process, including chemicals having different dipole moments.

In a preferred embodiment, processing unit 50 may take the form of a microcomputer or microcontroller, including a memory 52 for data storage. Processing unit 50 may also transmit control signals for the operation of other system elements, such as control means for controlling the production of a gas (e.g., a vaporization system), and/or for controlling the introduction of a gas into chamber 100 (e.g., a control valve or blower). Output unit 60 provides information in an audible and/or visual form. Accordingly, output unit 60 may take the form of an audio speaker and/or visual display unit.

Figure 2:
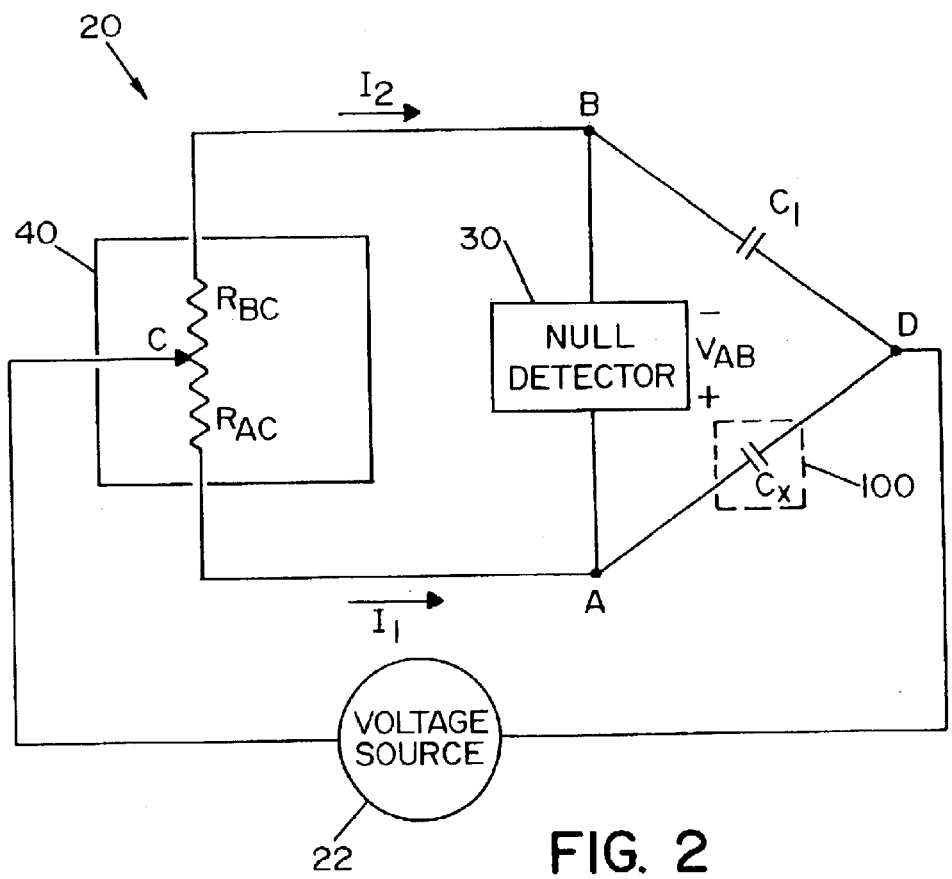
FIG. 2 is a schematic diagram illustrating a sensor circuit, according to a preferred embodiment of the present invention.

Referring now to FIG. 2, there is shown a detailed schematic of sensing circuit 20. In the preferred embodiment, sensor circuit 20 takes the form of a "bridge circuit." As is well known to those skilled in the art, bridge circuits are used to determine the value of an unknown impedance in terms of other impedances of known value. Highly accurate measurements are possible because a null condition is used to determine the unknown impedance. In the preferred embodiment, the bridge circuit is used to determine a capacitance value indicative of the concentration of a chemical component in a gas mixture. In the embodiment shown in FIG. 2, sensing circuit 20 is generally comprised of a voltage source 22, a null detector 30, an electronic potentiometer 40, a capacitor $C_1$ of known capacitance, and a capacitor $C_x$. Capacitor $C_1$ is a conventional capacitor located outside chamber 100, or is insulated from the gas mixture inside chamber 100. In a preferred embodiment, chamber 100 is an enclosed region.

Capacitor $C_x$ is directly exposed to a gas mixture. In this regard, capacitor $C_x$ is located inside chamber 100, wherein the gas mixture fills the gap between the conducting plates of capacitor $C_x$, thereby acting as an insulator or "dielectric" of capacitor $C_x$. Sensor circuit 20 provides data indicative of a capacitance $C_x$, corresponding to a chemical concentration. In this regard, capacitance $C_x$ will vary in accordance with changes in the concentration of chemical components in the gas mixture.

It should be appreciated that the gas mixture may not be the sole dielectric in the gap between the conducting plates of capacitor $C_x$. In this regard, it is contemplated that one or more solid dielectric materials may also be present in the gap, including, but not limited to, organic or inorganic materials.

In a preferred embodiment, capacitor $C_x$ is a parallel plate capacitor. However, it should be appreciated that capacitor $C_x$ could be constructed in a different form. For example, $C_x$ could be a cylindrical or spherical capacitor. If a spherical capacitor is used as capacitor $C_x$, holes must be placed in the outer shell of the capacitor such that the gas mixture can enter and exit the capacitor.

Electronic potentiometer 40 functions in the same manner as a mechanical potentiometer. In this regard, electronic potentiometer 40 is a three terminal device. Between two of the terminals is a resistive element. The third terminal known as the "wiper" is connected to various points along the resistive element. The wiper is digitally controlled by processing unit 50 (see FIG. 1). The wiper divides the resistive element into two resistors $R_{BC}$ and $R_{AC}$. Electronic potentiometer 40 may take the form of a digitally programmable potentiometer (DPP™) available from Catalyst Semiconductor, Inc. of Sunnyvale, Calif.

In a preferred embodiment, voltage source 22 provides an AC voltage signal, such as a sinusoidal or pulse waveform. Null detector 30 is a device for detecting a null condition (i.e., a short circuit), such as a galvanometer, a voltmeter, a frequency-selective amplifier, and the like.

Operation of sensor circuit 20 will now be described in detail. The elements of the bridge circuit are connected between junctions AC, BC, AD, and BD. Electronic potentiometer 40 is operated by processing unit 50 to vary the resistances $R_{BC}$ and $R_{AC}$ until the potential difference between junctions A and B ($V_{AB}$) is zero. When this situation exists, the bridge is said to be balanced or is "nulled." The following relationships then hold for voltages in the main branches:

$$V_{AC}=V_{BC}, \text{ and } V_{AD}=V_{BD},$$

where $V_{AC}$ is the voltage between junctions A and C, $V_{BC}$ is the voltage between junctions B and C, $V_{AD}$ is the voltage between junctions A and D, and $V_{BD}$ is the voltage between junctions B and D. Accordingly, $$V_{AD}/V_{AC}=V_{BD}/V_{BC}$$

$$V_{AD}=V_{BD}/(V_{AC}/V_{BC})$$

The capacitance of capacitor $C_x$ is connected between junctions A and D with a known capacitance of capacitor $C_1$ between junctions B and D. Electronic potentiometer 40, connected from junction A to junction C to junction B, is adjusted by processing unit 50 to vary the voltages $V_{AC}$ and $V_{BC}$.

When a null is detected by null detector 30, current $I_1$ flows from junction C to junction A to junction D, and a current $I_2$ flows from junction C to junction B to junction D. The voltage $V_{AC}$ across junctions A to C, and the voltage $V_{BC}$ across junctions B to C are:

$$V_{AC}=I_1R_{AC} \text{ and } V_{BC}=I_2R_{BC}.$$

The voltage across a capacitor with capacitance C, current I, and frequency $f$ is:

$$V = \frac{I}{2\pi f C}$$

Therefore, the voltages $V_{AD}$ and $V_{BD}$ may be expressed as:

$$V_{AD} = \frac{I_1}{2\pi f C_x}$$

$$V_{BD} = \frac{I_2}{2\pi f C_1}$$

As discussed above, $V_{AD}=V_{BD}/(V_{AC}/V_{BC})$, $V_{AC}=I_1R_{AC}$, and $V_{BC}=I_2R_{BC}$. Therefore, $$C_x = C_1\left(\frac{R_{BC}}{R_{AC}}\right).$$

In view of the forgoing relationship, when a null condition is detected, the resistance values for $R_{BC}$ and $R_{AC}$, along with the known capacitance value of capacitor $C_1$, can be used to determine unknown value of capacitance for capacitor $C_x$.

Chemical concentration detecting system 10 utilizes differences in dipole moments of different molecules to determine the relative concentration of a chemical component in a gas mixture. In the event there is only one chemical component in the gas mixture that has a measurable dipole moment, the concentration of the chemical component is determined. As discussed above, the gas mixture fills the gap between the conducting plates of capacitor $C_x$, thereby acting as a dielectric of capacitor $C_x$. By configuring capacitor $C_x$ as an element of a bridge circuit, a measure of resistance values $R_{AC}$ and $R_{BC}$, when the bridge is balanced or nulled, can be used to determine the capacitance of capacitor $C_x$. The capacitance of capacitor $C_x$ is indicative of the relative concentrations of chemical components in the gas mixture, since the permittivity of the respective dielectric is affected by the relative concentrations of the chemical components in the gas mixture.

It is well known that for a parallel plate capacitor $C=(k\epsilon_0)(A/d)=(\epsilon)(A/d)$, where C is capacitance, k is the dielectric constant, $\epsilon_0$ is the permittivity of free space ($8.85\times10^{-12}$ F/m), $\epsilon$ is the permittivity (Farads/meter) of the capacitor dielectric, A is the area of the capacitor plates (m$^2$), and d is the separation in meters between the capacitor plates. As $\epsilon$ increases, the capacitance C will increase. Where the capacitor is a parallel plate capacitor with circular plates of diameter D, $C=(\pi D^2 \epsilon)/(4d)$.

It will be appreciated that the dielectric constant k of the capacitor can be determined according to the following expression:

$$k = \frac{4dC}{\pi D^2 \varepsilon_0},$$

where the value of capacitance, C, is determined as discussed above. The dielectric constant of the capacitor can also be determined by determining the capacitance with the dielectric in place between the conducting plates ($C_d$), and then determine the capacitance without the dielectric in place ($C_o$). The ratio of the two capacitances equals the dielectric constant, $$k = \frac{C_d}{C_0}.$$

The response of a capacitor is influenced by the characteristics (e.g., frequency) of the AC waveform applied thereto. In this regard, capacitive reactance ($X_c$) is a function of frequency. Capacitive reactance is the opposition offered to the flow of alternating current by pure capacitance, and is expressed in ohms ($X_c=1/(2\pi f C)$). Accordingly, frequency of the waveform generated by voltage source 22 influences the response of capacitors. Thus, the frequency selected for voltage source 22 should preferably be a frequency that will provide a generally linear response for capacitance as the concentration of a chemical component in the gas mixture is varied. This will facilitate the use of interpolation and extrapolation of capacitance values, as will be discussed further below. If a suitable linear response is not obtained, then an expanded set of data points should be stored in memory 52.

Figure 3:
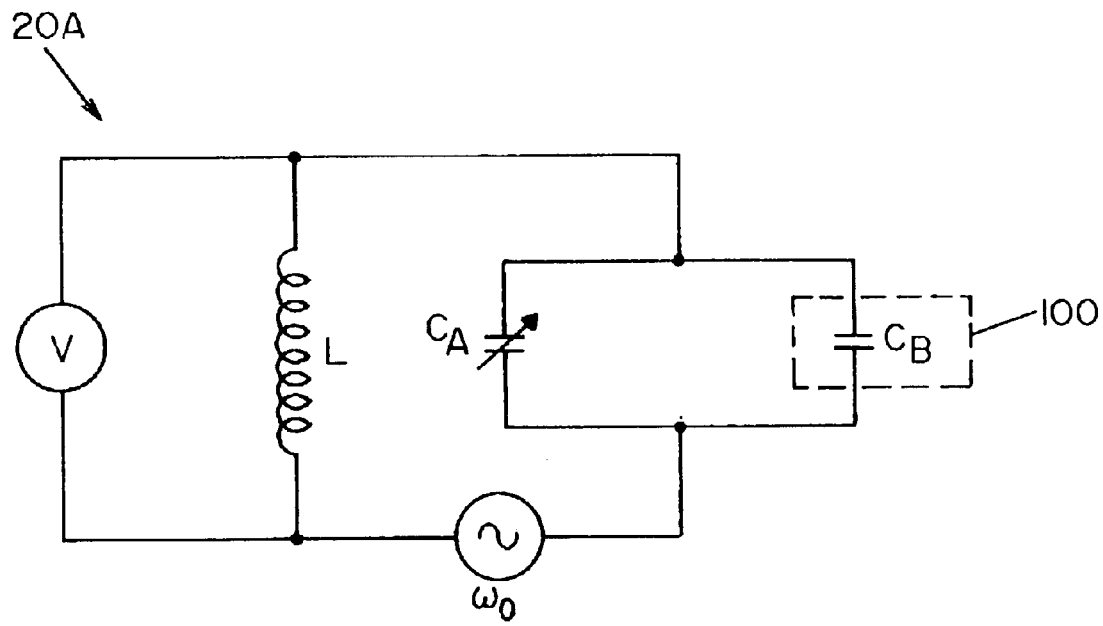
FIG. 3 is a schematic diagram illustrating a sensor circuit, according to an alternative embodiment of the present invention.

It should be appreciated that while one embodiment of the present invention includes a sensor circuit 20 in the form of a bridge circuit, other types of circuits and techniques (including other types of bridge circuits, and capacitance meters) known to those skilled in the art, may be suitably used to measure capacitance. For example, FIG. 3 illustrates an alternative sensor circuit 20A. Sensor circuit 20A is an LC resonant circuit, having a variable capacitor $C_A$ located outside chamber 100 (or otherwise isolated from the gas mixture inside chamber 100), and a capacitor $C_B$ directly exposed to the gas mixture. In this regard, capacitor $C_B$ is located in chamber 100, wherein the gas mixture fills the gap between the conducting plates of capacitor $C_B$, thereby acting as an insulator or "dielectric" of capacitor $C_B$. Since the resonance frequency $\omega_0=[L(C_A+C_B)]^{-1/2}$, the unknown capacitance of capacitor $C_B$ can be determined.

Figure 4:
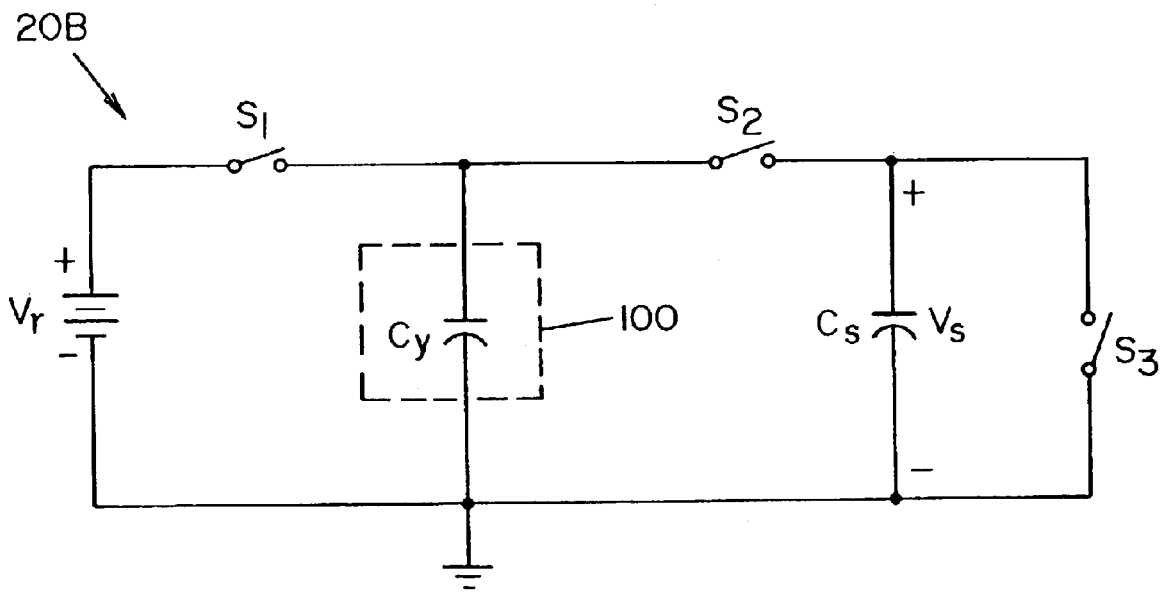
FIG. 4 is a schematic diagram illustrating a sensor circuit according to yet another alternative embodiment of the present invention.

FIG. 4 illustrates yet another alternative sensor circuit 20B suitable for use in connection with the present invention. Sensor circuit 20B is a "charge transfer" sensor circuit. Charge transfer sensor circuits are recognized to provide resolutions of fractions of a femtoFarad. In a charge transfer sensor circuit the unknown capacitance of a sense electrode is determined by charging the sense electrode to a fixed potential, and then transferring that charge to a charge detector comprising a capacitor of known capacitance. In sensor circuit 20B, capacitor $C_y$ of unknown capacitance is located in chamber 100, wherein the gas mixture fills the gap between the conducting plates of capacitor $C_y$, thereby acting as an insulator or "dielectric" of capacitor $C_y$. Capacitor $C_y$ is first connected to a DC reference voltage ($V_r$) via a switch $S_1$. Switch $S_1$ is reopened after $C_y$ is satisfactorily charged to the potential of $V_r$. Then, after as brief as possible a delay so as to minimize leakage effects caused by conductance, switch $S_2$ is closed and the charge (Q) present on $C_y$ is transferred to capacitor $C_s$ (i.e., the charge detector). Once the charge Q is satisfactorily transferred to capacitor $C_s$, switch $S_2$ is reopened. By reading voltage $V_s$, the capacitance of capacitor $C_y$ can be determined. $V_s$ may be input to an amplifier to provide the scaling necessary to present an analog-to-digital converter (ADC) with a useful range of voltage for digital processing. Switch $S_3$ acts as a reset means to reset the charge between charge transfer cycles, so that each charge transfer cycle has a consistent initial condition. Switches $S_1$, $S_2$ and $S_3$ may be electromechanical switches or transistors. Preferably, digital control logic is used to control switches $S_1$, $S_2$ and $S_3$. In a preferred embodiment, $C_s$ is selected to be significantly larger that $C_y$.

The equations governing sensor circuit 20B are as follows:

$V_s=V_r[C_y/(C_y+C_s)]$, therefore, $C_y=V_sC_s/[V_r-V_s]$.

It is recognized that in some cases, the capacitance of the capacitor exposed to the gas mixture located in chamber 100 may be in the range of femtoFarad capacitance to low picoFarad capacitance (e.g., 1 fF to 100 pF), and that changes in concentration of a chemical component in the gas mixture may only result in a change of capacitance in the range of low picoFarad capacitance or even femtoFarad capacitances. Accordingly, the sensor circuit used to measure capacitance may need to have high sensitivity to allow for measurement of small values of capacitance. One high sensitivity sensor circuit is the charge transfer sensor circuit described above. Other high sensitivity circuitry is provided by such devices as the PTL 110 capacitance transducer from Process Tomography Limited of Cheshire, United Kingdom. The PTL 110 measures small values of capacitance (up to 10 picoFarads) with a resolution of 1 femtoFarad. A 1616 Precision Capacitance Bridge from IET Labs, Inc. of Westbury, N.Y., allows for measurement of capacitances in the range from $10^{-7}$ pF to 10 $\mu$F. Tektronix produces the Tektronix 130 LC Meter that measures capacitance from 0.3 pF to 3 pF. It has also been acknowledged in the prior art literature that capacitance sensor circuits using modern operational amplifiers and analog-to-digital converters (ADCs) can easily obtain resolutions to 0.01 pF.

With reference to FIGS. 1 and 2, operation of chemical concentration detecting system 10, according to a preferred embodiment, will now be described in detail. As a preliminary step, processing unit 50 stores in memory 52 a set of data (i.e., data table) comprising values of the capacitance of capacitor $C_x$ for a plurality of relative concentrations of chemical components in a gas mixture. This set of data may be determined by exposing capacitor $C_x$ of system 10 to several different combinations of relative concentrations of chemical components, and recording the corresponding measured capacitance $C_x$.

For example, processing unit 50 may store values of the capacitance of capacitor $C_x$ that are determined for a plurality of relative concentrations of chemical components in a gas mixture, wherein the gas mixture includes at least one chemical component that is a decontaminant or sterilant, and air (at or below atmospheric pressure). As the relative concentrations of the chemical components are varied, the corresponding capacitance of capacitor $C_x$ is determined, and stored in memory 52. For instance, capacitance of capacitor $C_x$ may be determined for various relative concentrations of the chemical components. The recorded data corresponds with a curve associating capacitance to concentration.

In order to verify the accuracy of the data obtained using sensor circuit 20, it may be advisable to use an analytical tool to accurately measure concentrations of chemical components in the gas mixture. In this manner, only verified data is stored in memory 52. The analytic tool is preferably selected by the concentration ranges, size of region defined by chamber 100, desired response time, and duration of measurement. One analytic tool for use with measuring concentrations of a chemical component (e.g., vaporized hydrogen peroxide) is Fourier Transform Infra Red (FTIR) spectroscopy, or a high quality near-infrared (NIR) spectroscopy.

After the set of data is stored in memory 52, measurement of the concentration of a chemical component in the gas mixture can commence. Capacitor $C_x$ is exposed to a gas mixture that is being monitored. As indicated above, capacitor $C_x$ may be located in an enclosed chamber 100 filled with a gas mixture. A determination of $R_{AC}$ and $R_{BC}$ when the bridge is nulled is then used to determine a value for the capacitance of capacitor $C_x$. As discussed above, $C_x = C_1 (R_{BC}/R_{AC})$. A linear relationship between concentration and capacitance allows one to normalize any measurement made so as to provide the absolute concentration of each chemical component in the gas mixture.

When determining the concentration of an unknown, once the capacitance is measured, the data stored in memory 52 is searched for the capacitance of capacitor $C_x$ to obtain the corresponding relative concentrations. If the capacitance of capacitor $C_x$ is not found in the pre-stored data, the stored data may be interpolated or extrapolated to obtain a concentration corresponding to the measure capacitance of capacitor $C_x$. As noted above, frequency of the waveform generated by voltage source 22 will influence the response of capacitors. Where the capacitance of capacitor $C_x$ does not exhibit a suitable linear response, an expanded set of data points should be stored in memory 52, so that interpolation or extrapolation is unnecessary.

It should be appreciated that while a preferred embodiment of the present invention uses a measure of a capacitor's capacitance to determine relative concentrations, it is also contemplated that a measure of other electrical properties of a capacitor may be used to determine relative concentrations, including, but not limited to, voltage, charge, reactance, current, permittivity, and dielectric constant.

Based upon the determined relative concentrations, processing unit 50 may be programmed to output control signals for modifying relative concentrations. For instance, processing unit 50 may transmit control signals (see FIG. 1) for controlling the production of a gas (e.g., a vaporization process), and/or for controlling the introduction of a gas into chamber 100, thereby modifying the relative concentrations. Accordingly, processing unit 50 may provide feedback control to adjust the relative concentrations to correspond with desired relative concentrations that provide optimum decontamination. Processing unit 50 may also output signals to output unit 60 to provide an audible and/or visual indicator when the determined relative concentrations are not within a desired range. The visual indicator may assist an operator by including a display of the relative concentrations or absolute concentration of an oxidant or sterilant as determined by processing unit 50.

As indicated above, the gas mixture inside chamber 100 may include chemical components that are decontaminants or sterilants, such as antimicrobial chemicals, and chemical components that are base chemicals (i.e., diluents for an antimicrobial chemical, or vehicles or carriers for an antimicrobial chemical).

Examples of antimicrobial chemicals include, but are not limited to, vaporized hydrogen peroxide, vaporized bleach, vaporized peracid, vaporized peracetic acid, ozone, ethylene oxide, halogen containing compounds, ammonia gas, other gaseous oxidants, and mixtures thereof. The halogens of the halogen containing compounds include, but are not limited to, chlorine and fluorine.

Examples of base chemicals include, but are not limited to, de-ionized water vapor, distilled water vapor, a vaporized alcohol (e.g., a tertiary alcohol), and mixtures thereof.

Some typical examples of sterilizing atmospheres that may be created and whose concentrations or relative concentrations can be measured include, but are not limited to: ozone; vaporized hydrogen peroxide and water vapor; ethylene oxide; vaporized hydrogen peroxide, water vapor and ozone; vaporized hydrogen peroxide, water vapor and ethylene oxide; ozone and ethylene oxide; and vaporized hydrogen peroxide, water vapor, ozone and ethylene oxide.

In an alternative embodiment of the present invention, two sensor circuits 20 are used. Capacitor $C_{x1}$ of the first sensor circuit 20 is exposed to a gas mixture including (1) a first chemical component that is an antimicrobial chemical (e.g., vaporized hydrogen peroxide), (2) a second chemical component that is a base chemical (e.g., water vapor), and (3) air. Capacitor $C_{x2}$ of the second sensor circuit 20 is exposed only to the second chemical component and the air. Processing unit 50 calculates the difference between the two measured capacitances $C_{x1}$ and $C_{x2}$ to determine the concentration of the first chemical component. In this regard, the difference in capacitances $C_{x1}$ and $C_{x2}$ will be attributable to the concentration of the first chemical component of the decontaminant.

Other modifications and alterations will occur to others upon their reading and understanding of the specification. It is intended that all such modifications and alterations be included insofar as they come within the scope of the invention as claimed or the equivalents thereof.

Having described the invention, the following is claimed:

1. A chemical concentration detecting system for determining a concentration of a first chemical component in a gas mixture, comprising:

sensing means responsive to changes in the concentration of the first chemical component in the gas mixture, said sensing means including a capacitor having first and second conducting elements exposed to the gas mixture, wherein said gas mixture comprises a dielectric therebetween, said capacitor having an electrical property that varies according to the concentration of the first chemical component in the gas mixture;

a memory for storing a set of data including (a) property values associated with the electrical property and (b) concentration values corresponding with said property values that are indicative of the relative concentration of the first chemical component in the gas mixture; and processing means receiving data from the sensing means and determining the relative concentration of the first chemical component in the gas mixture by accessing the set of data stored in the memory.

2. A chemical concentration detecting system according to claim 1, wherein said first capacitor is selected from the group consisting of: a parallel plate capacitor, a cylindrical capacitor, and a spherical capacitor.

3. A chemical concentration detecting system according to claim 1, wherein said processing means determines a relative concentration of the first chemical component in the gas mixture using said property values to locate corresponding concentration values stores in said memory.

4. A chemical concentration detecting system according to claim 1, wherein said processing means interpolates or extrapolates said set of data to determine the relative concentration of the first chemical component in the gas mixture.

5. A chemical concentration detecting system according to claim 1, wherein said processing means normalizes said relative concentration to provide an absolute concentration of said first chemical component in the gas mixture.

6. A chemical concentration detecting system according to claim 1, wherein said first chemical component is an antimicrobial chemical.

7. A chemical concentration detecting system according to claim 6, wherein said antimicrobial chemical is a gaseous oxidant.

8. A chemical concentration detecting system according to claim 6, wherein said antimicrobial chemical is selected from a group consisting of: vaporized hydrogen peroxide, vaporized peracid, vaporized peracetic acid, vaporized bleach, ozone, ethylene oxide, ammonia gas, a halogen containing compound, and mixtures thereof.

9. A chemical concentration detecting system according to claim 8, wherein said halogen containing compound is selected from the group consisting of: chlorine and fluorine.

10. A chemical concentration detecting system according to claim 6, wherein said gas mixture includes a second chemical component that is a base chemical.

11. A chemical concentration detecting system according to claim 10, wherein said base chemical is at least one of: (a) a diluent for said antimicrobial chemical, and (b) a vehicle for said antimicrobial chemical.

12. A chemical concentration detecting system according to claim 10, wherein said base fluid is selected from a group consisting of: de-ionized water vapor, distilled water vapor, a vaporized alcohol, and mixtures thereof.

13. A chemical concentration detecting system according to claim 12, wherein said vaporized alcohol is a tertiary alcohol.

14. A chemical concentration detecting system according to claim 1, wherein said system means further comprises:

a bridge circuit, wherein said capacitor forms a part of the bridge circuit.

15. A chemical concentration detecting system according to claim 1, wherein said sensing means further comprises: a charge transfer sensor circuit, wherein said capacitor forms a part of the charge transfer sensor circuit.

16. A method for determining a concentration of a first chemical component in a gas mixture, comprising:

exposing a capacitor, having first and second conducting elements, to the gas mixture, wherein said gas mixture comprises a dielectric therebetween, said capacitor having an electrical property that varies according to the concentration of the first chemical component in the gas mixture;

pre-storing data including electrical property values associated with said electrical property of said capacitor and concentration values corresponding with said electrical property values that are indicative of the relative concentration of the first chemical component in said gas mixture determining an electrical property value associated with the capacitor; and accessing said memory using said electrical property value to determine the relative concentration of the first chemical component in the gas mixture.

17. A method according to claim 16, wherein said step of accessing said memory to determine the relative concentration of the first chemical component in said gas mixture includes:

using said electrical property values to locate corresponding concentration values.

18. A method according to claim 16, wherein said method further comprises:

interpolating or extrapolating the pre-stored data to determine the relative concentration of the first chemical component in said gas mixture.

19. A method according to claim 16, wherein said method further comprises:

normalizing said relative concentration to provide an absolute concentration of the first chemical component in said gas mixture.

20. A method according to claim 16, wherein said first chemical component is an antimicrobial chemical.

21. A method according to claim 20, wherein said antimicrobial chemical is a gaseous oxidant.

22. A method according to claim 21, wherein said antimicrobial chemical is selected from a group consisting of: vaporized hydrogen peroxide, vaporized peracid, vaporized peracetic acid, vaporized bleach, ozone, ethylene oxide, ammonia gas, a halogen containing compound, and mixtures thereof.

23. A method according to claim 22, wherein said halogen containing compound is selected from the group consisting of: chlorine and fluorine.

24. A method according to claim 16, wherein said gas mixture includes a second chemical component that is a base chemical.

25. A method according to claim 24, wherein said base chemical is at least one of: (a) a diluent for said antimicrobial chemical, and (b) a vehicle for said antimicrobial chemical.

26. A method according to claim 24, wherein said base fluid is selected from a group consisting of: de-ionized water vapor, distilled water vapor, a vaporized alcohol, and mixtures thereof.

27. A method according to claim 26, wherein said alcohol is a tertiary alcohol.

28. A method for determining a concentration of a first chemical component in a gas mixture including at least two antimicrobial chemicals, comprising:

exposing a capacitor, having first and second conducting elements, to the gas mixture, wherein said gas mixture comprises a dielectric therebetween, said capacitor having an electrical property that varies according to the concentration of the first chemical component in the gas mixture;

pre-storing data including electrical property values associated with said electrical property of said capacitor and concentration values corresponding with said electrical property values that are indicative of the relative concentration of the first chemical component in said gas mixture determining an electrical property value associated with the capacitor; and accessing said memory using said electrical property value to determine the relative concentration of the first chemical component in the gas mixture.

29. A method according to claim 28, wherein said gas mixture further includes a base chemical.

30. A method according to claim 29, wherein said at least two antimicrobial chemicals include vaporized hydrogen peroxide and ozone, and said base chemical is water vapor.

31. A method according to claim 29, wherein said at least two antimicrobial chemicals include ozone and ethylene oxide, and said base chemical is water vapor.

* * * * *